US 6,562,366 B2

(12) United States Patent
Cook et al.

(10) Patent No.: US 6,562,366 B2
(45) Date of Patent: May 13, 2003

(54) METHOD TO PREVENT THE FORMATION AND ENHANCE THE BREAKDOWN OF BEZOARS IN ANIMALS AND HUMANS

(75) Inventors: Mark E. Cook, Madison, WI (US); Beth M. Drake, Sycamore, IL (US); Leonard S. Girsh, Palm Beach, FL (US); Janet R. Jackson, Columbia, IL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/839,892

(22) Filed: Apr. 20, 2001

(65) Prior Publication Data

US 2002/0182202 A1 Dec. 5, 2002

(51) Int. Cl.$^7$ ............................................... A61K 47/00
(52) U.S. Cl. ..................... 424/439; 424/400; 424/438; 424/442
(58) Field of Search ................................ 424/400, 438, 424/439, 442

(56) References Cited

U.S. PATENT DOCUMENTS 6,080,403 A    6/2000   Shields, Jr. et al.

2001/0046693 A1 * 11/2001 Beek et al. .................. 435/183

OTHER PUBLICATIONS

Qureshi, NH et al., "Trichobezoar—a condition to think of in case of mobile abdominal mass," Irish Medical Journal 85: 74 (1992).

* cited by examiner

*Primary Examiner*—Carlos Azpuru
*Assistant Examiner*—Charesse Evans
(74) *Attorney, Agent, or Firm*—Quarles & Brady LLP

(57) ABSTRACT

A digestive system bezoar in a human or non-human animal susceptible to bezoar formation can be reduced in size by administering to the animal a food grade agent for emulsifying fat in an amount sufficient to reduce the size of the bezoar so that the bezoar can pass out of the animal's digestive system. In a similar method for preventing bezoar formation in a human or non-human animal susceptible to bezoar formation, a food grade agent for emulsifying fat can be administered to the animal in an amount sufficient to prevent formation of bezoars, or at least to prevent formation of bezoars larger than a size that becomes trapped in the animal's digestive system.

25 Claims, No Drawings

METHOD TO PREVENT THE FORMATION AND ENHANCE THE BREAKDOWN OF BEZOARS IN ANIMALS AND HUMANS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to methods for preventing gastrointestinal bezoar formation and for reducing the size of a gastrointestinal bezoar in humans and non-human animals. Bezoars are any of several types of solid or semi-solid masses of indigestible material found in the stomach of humans and many animals including cattle, cats, rats, rabbits, and non-human primates. Trichobezoars contain a mesh of ingested hair; phytobezoars contain fruit or vegetable matter. Other combinations of indigestible materials such as plastic bags are also known. Trichobezoars are known to entrap undigested dietary fat in the hair mesh. Qureshi, N. H., et al., "Trichobezoar—a condition to think of in case of mobile abdominal mass," *Irish Med. J.* (June 1992). While the incidence of bezoars is generally very low in humans, a somewhat greater risk exists among mentally retarded or emotionally disturbed children, particularly humans who habitually pluck their hair (trichotillomania) and/or eat their hair (trichophagia). Bezoars are commonly referred to as "hairballs" and the terms will be used interchangeably throughout this application.

Bezoars typically do not pass through the intestines unless treated or surgically removed. Sometimes small bezoars can be removed from an internal passageway through a scope placed through the mouth and into the stomach. Non-surgical remedies include fiber-supplemented feed and petroleum-Jelly based oral medicament for lubricating the internal passageway. These remedies can soften a bezoar, but do not actually break it up. Bezoars can become impacted if the treatment does not sufficiently soften the hairball. U.S. Pat. No. 6,080,403 describes a protease-containing hairball remedy and method for using the same. However, accumulated fat can undesirably interfere with proteolytic or acid hydrolysis by preventing aqueous gastric components (e.g., proteases and gastric acids) from contacting the hairball.

Reliable non-surgical methods for reducing the size of bezoars and for preventing their occurrence are needed, as the existing methods are relatively ineffective.

BRIEF SUMMARY OF THE INVENTION

The present invention is summarized in that a method for reducing the size of a gastrointestinal bezoar in a human or non-human animal susceptible to bezoar formation includes the step of administering to the animal a food grade agent for emulsifying fat in an amount sufficient to reduce the size of the bezoar so that the bezoar can pass out of the animal's digestive system. In a similar method for preventing bezoar formation in a human or non-human animal susceptible to bezoar formation, a food grade agent for emulsifying fat is administered to the animal in an amount sufficient to prevent formation of bezoars, or at least to prevent formation of bezoars at or above a size that becomes trapped in the animal's digestive system.

It is an object of the invention to reduce the occurrence and severity of bezoars in human and non-human animals.

It is a feature of the invention that the undigested fat trapped in the bezoar mesh is digested by an agent for emulsifying fat.

It is an advantage of the invention that agents useful in the method are available as inexpensive food-grade ingredients, so that adding the agents to an animal's diet adds little cost to the final food or feed product.

Other objects, advantages and features of the invention will become apparent upon consideration of the following detailed description of the invention.

BRIEF DESCRIPTION OF THE SEVERAL VIEWS OF THE DRAWINGS

Not applicable.

DETAILED DESCRIPTION OF THE INVENTION

The fat content of a bezoar, particularly a trichobezoar, can exceed about 20% by dry weight. The inventors here demonstrate that treating a hairball with a food grade fat emulsifying agent can reduce hairball size by degrading the enmeshed fat. From this observation, a skilled artisan will appreciate that treatment of a hairball in the stomach of a human or non-human animal with a food grade fat emulsifying agent can reduce its size and permit the hairball to pass from the animal's digestive system without requiring surgical or endoscopic intervention.

In general, the present invention provides a method of using food grade fat emulsifiers to reduce the size of any bezoar that comprises enmeshed undigested fat and thereby enhance the breakdown of the bezoar by orally administering to a human or non-human animal a food grade fat emulsifying agent at an amount effective to reduce the size of the bezoar. The bezoar can be in its early formation stage or can be fully formed. In the former case, the reduction method can function to prevent the formation of full size bezoars such that the human or non-human animal may never note the existence of a bezoar. In the latter case, the reduction method can function therapeutically to reduce the impact of a bezoar on the animal.

Any food grade fat emulsifier can be used. The fat emulsifier can be a food grade surfactant including various soaps and various detergents such as a Tween surfactant, preferably Tween 20 or Tween 80, most preferably Tween 80, lecithin such as phosphotidyl choline, and bile salts. Such fat emulsifier can also be an enzyme that degrades lipids or fats, such as a lipase which includes but is not limited to lipoprotein lipases, hormone sensitive lipases and phospholipase. Two or more different fat emulsifiers can be combined for use in the methods of the invention.

The amount of the fat emulsifying agent to be administered will vary depending upon the extent of treatment desired, but should generally be between about 0.01% and 5% of the diet by weight to reduce the size of a fully formed bezoar, more preferably between about 0.1% and 2% by weight, and most preferably about 1% by weight. Amounts greater than about 5% are considered no more effective than lower amounts, but are not considered to be harmful to the subject.

A bezoar need not be completely degraded to consider the method a success. It is sufficient that a bezoar is broken down into pieces of sufficiently small size to pass through the animal's digestive tract. In some cases, it may even be adequate for the bezoar to be reduced in size only enough to relieve discomfort.

The present invention also includes a method for reducing accumulation of undigested dietary fat in a forming bezoar. The method can be, but need not be, sufficiently effective as to completely prevent bezoar formation. Such methods include the step of administering to the animal a food-grade fat emulsifier as described above at an amount sufficient to reduce or prevent undigested dietary fat from becoming enmeshed in the bezoar mesh. The amount administered is sufficient if the fat either cannot accumulate in a forming bezoar or accumulates to a reduced extent than in an untreated human or non-human animal. When the amount of fat enmeshed in a bezoar is reduced, the components of the hairball can be more readily dispersed. For such prophylactic bezoar prevention methods, the above-mentioned fat emulsifier amounts for treatment can be effective, though even lower concentrations of a fat emulsifier, in the range of 0.001% to 1% by weight, more preferably in the range of 0.01% to 0.1% by weight, can also be used.

The present invention also includes a method for reducing the size of a bezoar by using a fat emulsifier in combination with an exogenously administered protease. The fat emulsifier makes the hairball more readily dispersed while the protease breaks down the protein matrix.

In the following example, the applicants simulated in vitro the conditions found in a human or non-human animal stomach (pH 3.0, 100° F. for a fixed period of time, here 24 hours) to demonstrate the effect on a hairball of varying amounts of a fat-emulsifying agent. The examples demonstrates that the treatment emulsified the enmeshed fat and degraded the hairball to a lesser or greater extent depending on the concentrations of the agent used, up to a plateau level.

EXAMPLE

Tween 80 (lot#1373A, Uniqema, Wilmington, Del.) was dissolved in 150 ml acidified water (pH 3.0) at a concentration of 0%, 5%, 10%, 15%, and 20%. A feline hairball (1.0–1.1 g) was then added to each of the five solutions. The mixtures were incubated at 100° F. for 24 hours. After incubation, hair lumps (defined as hair not floating free in the liquid) was removed and the liquid was strained through cheesecloth. Free hair and hair lumps were then dried and weighed.

| % Tween-80 | Hair clump wt (g) (% total wt) | Free hair wt (g) (% total wt) | % enhanced break down |
|---|---|---|---|
| 0 | 0.6238 (84.46%) | 0.1148 (15.54%) | — |
| 5 | 0.6273 (79.62%) | 0.1606 (20.38%) | 5 |
| 10 | 0.2214 (46.22%) | 0.2576 (53.78%) | 35 |
| 15 | 0.2157 (52.14%) | 0.1980 (47.86%) | 35 |
| 20 | 0.2290 (48.00%) | 0.2480 (51.99%) | 35 |

We claim:

1. A method for reducing the size of a gastrointestinal bezoar that comprises enmeshed undigested fat in a human or non-human animal, the method comprising the step of:
    orally administering to the animal a food grade fat emulsifying agent in an amount that reduces the enmeshed fat in the bezoar.

2. The method of claim 1 wherein the bezoar treated in the method is fully formed.

3. The method of claim 1 wherein the bezoar treated in the method is not fully formed.

4. The method of claim 1, wherein the fat emulsifying agent is a lipase.

5. The method of claim 4, wherein the lipase is selected from the group consisting of lipoprotein lipases, hormone sensitive lipases and phospholipases.

6. The method of claim 1, wherein the fat emulsifying agent is a surfactant.

7. The method of claim 6, wherein the surfactant is selected from the group consisting of detergents, lecithins, and bile salts.

8. The method of claim 6, wherein the surfactant is Tween.

9. The method of claim 8, wherein the surfactant is selected from the group consisting of Tween 20 and Tween 80.

10. The method of claim 8, wherein the surfactant is Tween 80.

11. The method of claim 7, wherein the lecithin is phosphotidyl choline.

12. The method of claim 1, wherein the fat emulsifying agent comprises at least two agents.

13. The method of claim 1, wherein the fat emulsifying agent is administered in the diet at about 0.01% to about 5% by weight.

14. The method of claim 13, wherein the fat emulsifying agent is administered in the diet at about 0.1% to about 2% by weight.

15. The method of claim 13, wherein the fat emulsifying agent is administered in the diet at about 1% by weight.

16. The method of claim 13, wherein the fat emulsifying agent is administered in the diet at about 0.001% to about 1% by weight.

17. The method of claim 13, wherein the fat emulsifying agent is administered in the diet at about 0.01% to about 0.1% by weight.

18. The method of claim 1, wherein the non-human animal is selected from the group consisting of cattle, cats, rats, rabbits and non-human primates.

19. The method of claim 1, wherein the non-human animal is a cat.

20. The method of claim 1, wherein the bezoar is a trichobezoar.

21. The method of claim 1, wherein the bezoar is a phytobezoar.

22. The method of claim 1, further comprising the step of:
    orally administering to the animal a protease in an amount sufficient to break down a protein matrix in the bezoar.

23. A method for reducing the size of a gastrointestinal bezoar that comprises enmeshed undigested fat in a human or non-human animal, the method comprising the step of:
    orally administering to the animal a food grade fat emulsifying agent in an amount that reduces the enmeshed fat in the bezoar, wherein the fat emulsifying agent is a surfactant and wherein the surfactant is Tween.

24. The method of claim 23, wherein the surfactant is selected from the group consisting of Tween 20 and Tween 80.

25. The method of claim 23, wherein the surfactant is Tween 80.

* * * * *